United States Patent [19]
Rueter et al.

[11] Patent Number: 5,441,524
[45] Date of Patent: Aug. 15, 1995

[54] ENERGY EFFICIENT MULTIPLE SENSOR CARDIAC PACEMAKER

[75] Inventors: John C. Rueter, Shoreview, Minn.; Bruce L. Wilkoff, South Russell, Ohio

[73] Assignee: Medtronic, Inc., Minneapolis, Minn.

[21] Appl. No.: 113,950

[22] Filed: Aug. 30, 1993

[51] Int. Cl.⁶ ............................................ A61N 1/362
[52] U.S. Cl. .................................................. 607/18
[58] Field of Search .................. 607/7, 17, 18, 28, 19, 607/20

[56] References Cited

U.S. PATENT DOCUMENTS

| | | | |
|---|---|---|---|
| 4,257,423 | 3/1981 | McDonald et al. | 128/419 |
| 4,305,397 | 12/1981 | Weisbrod et al. | 128/419 |
| 4,323,074 | 4/1982 | Nelms | 128/419 |
| 4,379,459 | 4/1983 | Stein | 128/419 |
| 4,428,378 | 1/1984 | Anderson et al. | 128/419 |
| 4,476,868 | 10/1984 | Thompson | 128/419 |
| 4,485,813 | 12/1984 | Anderson et al. | 128/675 |
| 4,527,568 | 7/1985 | Rickards | 128/419 |
| 4,550,370 | 10/1985 | Baker | 364/413 |
| 4,556,063 | 12/1985 | Thompson et al. | 128/419 |
| 4,702,253 | 10/1987 | Nappholz et al. | 128/419 |
| 4,770,177 | 9/1988 | Schroeppel | |
| 4,860,751 | 8/1989 | Callaghan . | |
| 4,905,697 | 3/1990 | Heggs et al. | 128/419 |
| 4,926,863 | 5/1990 | Alt | 128/419 |
| 4,979,507 | 12/1990 | Heinz et al. | 128/419 |
| 5,003,976 | 4/1991 | Alt | 607/18 |
| 5,101,824 | 4/1992 | Lekholm | 128/419 |
| 5,127,404 | 7/1992 | Wybomy et al. | 128/419 |
| 5,158,078 | 10/1992 | Bennett . | |
| 5,271,359 | 12/1993 | Wahlstrand . | |

FOREIGN PATENT DOCUMENTS 0191404  8/1986  European Pat. Off. ............ 607/18

OTHER PUBLICATIONS

"Erfahrungen Mit Einem Zweisensorgesteuerten Frequenzadaptierenden Schrittmachersystem" by Heuer et al. (1986).

*Primary Examiner*—William E. Kamm
*Assistant Examiner*—Marianne Parker
*Attorney, Agent, or Firm*—Harold R. Patton

[57] ABSTRACT

A multiple sensor cardiac pacemaker blends the outputs from a fast-reacting Activity sensor and a slower-reacting Minute Ventilation sensor to achieve an optimally desirable pacing rate. The pacemaker conserves battery energy by forcing the Minute Ventilation sensor output to be at its minimum value by disabling the Minute Ventilation algorithm for a predetermined time period when the Activity sensor is at its minimum observed value. Power is conserved because the Minute Ventilation sensor and associated algorithms which normally consume power to operate the circuitry, and to measure impedance are disabled temporarily only during selected periods where the Activity sensor is at its minimum observed value, thereby maintaining optimal blending of the pacemaker sensor outputs in achieving the desired pacing rates.

22 Claims, 3 Drawing Sheets

ENERGY EFFICIENT MULTIPLE SENSOR CARDIAC PACEMAKER

BACKGROUND OF THE INVENTION

1. Field of the Invention

The present invention relates implanted battery operated cardiac pacemakers employing battery energy saving features, and more particularly, it relates to means and methods for controlling one pacemaker sensor by another pacemaker sensor to maximize conservation of battery energy.

2. Description of the Prior Art

Rate responsive pacemaker systems are widely available in the art. Rate responsive systems contain means for monitoring at least one patient variable and for determining an indicated pacing rate as a function of such sensed pacing variable, so as to control pacing rate optimally in terms of the patient condition. Such rate responsive pacemakers have gained wide acceptance as providing an improved response to the patient's physiological needs, as compared to programmable fixed rate pacemakers.

A number of patient variables or rate control parameters have been suggested in the technical literature and used commercially. One physiological parameter utilized for rate control is patient activity level. Activity sensors have been widely utilized for detecting the general activity level of a patient with a pacemaker, and for controlling the pacing rate or escape interval in response to detected activity level such as that disclosed in U.S. Pat. No. 4,428,378 issued to Anderson et al. and assigned to the assignee of the present invention and which is incorporated herein by reference in its entirety.

Recent approaches to optimizing rate responsiveness use dual or plural sensors, in order that the drawbacks or deficiencies of a given sensor and/or algorithm may be compensated by the use of a second or other sensors having different characteristics. This approach is set forth in U.S. Pat. No. 4,527,568 issued to Rickards, which discloses switching control of rate responsiveness from one monitored parameter to another control parameter. There are many other examples of multiple sensor approaches in the literature, and reference is made to U.S. Pat. Nos. 5,101,824, 4,926,863 and 4,905,697. These references are characterized by designs which switch control from one sensor to another, or from one algorithm to another, depending upon monitored values of the rate control parameters.

Many rate responsive, multiple sensor cardiac pacemakers, including some of those discussed above, achieve a reduction in energy consumption in order to improve battery longevity, through the use of rate optimization. In addition, energy saving circuitry measures have reduced the pacemaker's power consumption. The development of modern electrodes that build up very small polarization voltages has also contributed to reducing the energy required for pacing. In U.S. Pat. No. 4,979,507 to Heinz et al., an energy saving cardiac pacemaker is disclosed which is based on optimizing stimulus thresholds. However, none of the above multiple sensor cardiac pacemaker art discloses controlling one physiological sensor with another physiological sensor for the purpose of minimizing battery energy consumption without impairment of the blending of multiple sensor outputs to produce a composite optimal heart rate.

SUMMARY OF THE INVENTION

Algorithms have been developed for the blending of the outputs of two or more sensors to produce a composite heart rate for cardiac pacemakers. All such algorithms produce composites whose values are within the superset of the bounds of the rates that would have been chosen by each sensor individually. Because of this bounding, when one sensor calls for a pacing rate at one of the combined sensor extremes, the additional information provided by any additional sensors can mediate that outcome, but cannot cause pacing at a rate slower than the minimum or faster than the maximum.

In the particular case of a fast-reacting sensor such as an Activity sensor and a slower-reacting sensor such as a Minute Ventilation (MV) sensor (as measured by the impedance of transthoracic or other vectors), there is opportunity to disable the slower-moving sensor when the sensors agree that the pacing rate should be at its minimum, or at its maximum. A present implementation of a MV algorithm, is disclosed in U.S. Pat. No. 5,271,395 issued Wahlstrand et al. entitled "Method And Apparatus For Rate-Responsive Cardiac Pacing", filed 17 Apr. 1992 and assigned to the assignee of the present invention and is incorporated by reference in its entirety herein. This implementation of a MV algorithm incorporates a running average known as-the "long-term average" representing approximately 34 minutes. When this value reaches its minimum or maximum, the patient must have been breathing slowly or rapidly for approximately one-half hour. The most likely scenario is a patient asleep.

A sleeping patient whose Activity sensor indicates essentially no instantaneous activity, and whose long-term average of Minute Ventilation is at baseline, needs the minimum programmed pacing rate. The MV sensor is likely to add no information as long as the Activity sensor is at baseline. Any input from the MV sensor at this point would be expected to be slow-moving.

The MV sensor and associated algorithms consume power to operate the circuitry, power delivered across a dipole for measuring the impedance, and power to operate the microprocessor performing calculations (when the microprocessor would otherwise have been in standby mode drawing no power). Therefore, the present invention provides a method of saving power without degradation of the multiple-sensor behavior. The inventive method can best be understood by recognizing that the current method of operating the MV sensor requires digitizing raw electrical values every two seconds. These values are used for updating short-term and long-term averages, and deriving pacing rates. The inventive method, in order to conserve battery energy, disables the MV sensor during chosen times i.e., total cessation of all MV-related sample collection and processing, or forcing baseline values onto the short-term and long-term averages without having collected data samples when the Activity sensor is at baseline.

Other features and advantages of the present invention will be set forth in, or become apparent from, the following description and claims and illustrated in the accompanying drawings, which disclose by way of example and not by way of limitation, the principle of the invention and the structural implementation of the inventive concept.

BRIEF DESCRIPTION OF THE DRAWINGS

The foregoing and other features of the present invention will be best appreciated with reference to the detailed description of a specific embodiment of the invention, which follows, when read in conjunction with accompanying drawings, wherein.

DETAILED DESCRIPTION OF A SPECIFIC EMBODIMENT OF THE INVENTION

Figure 1:
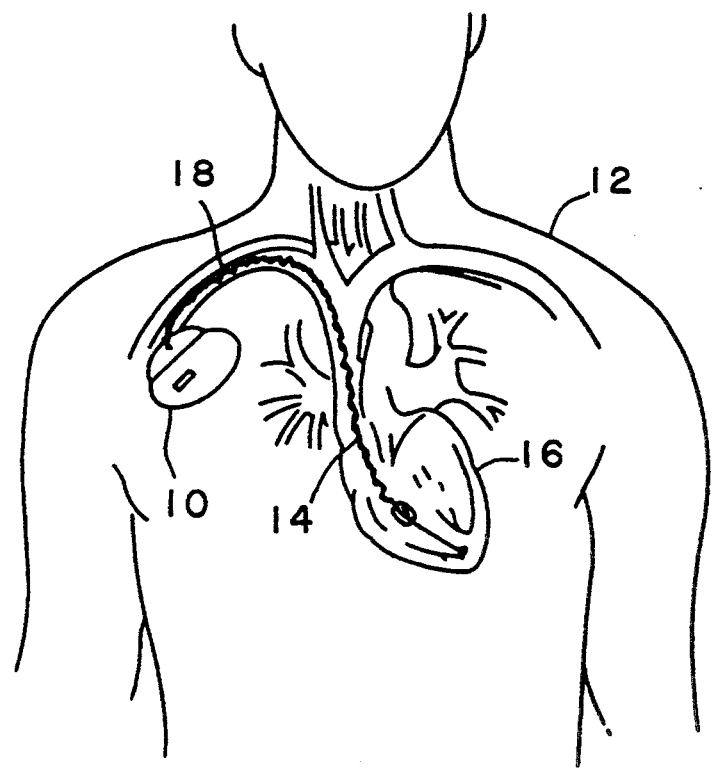
FIG. 1 is a diagram showing the placement in a patient of a pacemaker in accordance with one embodiment of the present invention.

FIG. 1 shows generally where a pacemaker 10 in accordance with one embodiment of the present invention may be implanted in a patient 12. It is to be understood that pacemaker 10 is contained within a hermetically-sealed, biologically inert outer shield or "can", in accordance with common practice in the art. A pacemaker lead 14 is electrically coupled to pacemaker 10 and extends into the patient's heart 16 via a vein 18. The distal end of lead 14 includes on or more exposed conductive electrodes for receiving electrical cardiac signals and/or for delivering electrical pacing stimuli to the heart 16. Lead 14 may be implanted with its distal end situated in the atrium or ventricle of heart 16.

Figure 2:
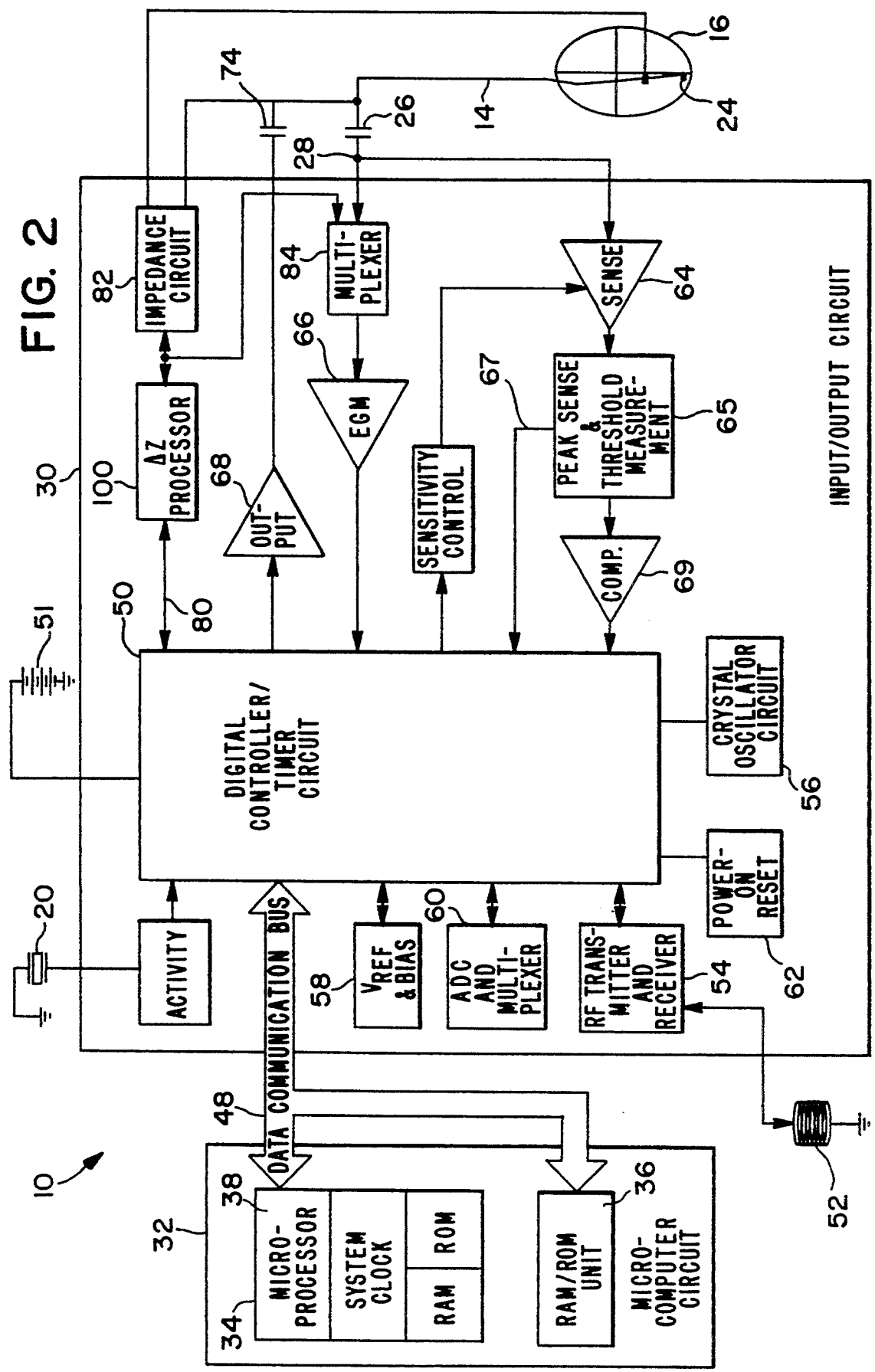
FIG. 2 is a block diagram of functional components of the pacemaker of FIG. 1.

Turning now to FIG. 2, a block diagram of pacemaker 10 from FIG. 1 is shown. Although the present invention will be described herein in conjunction with a pacemaker 10 having a microprocessor-based architecture, it will be understood that pacemaker 10 may be implemented in any logic based, custom integrated circuit architecture, if desired. It will also be understood that the present invention may be utilized in conjunction with other implantable medical devices, such as cardioverters, defibrillators, cardiac assist systems, and the like.

In the illustrative embodiment shown in FIG. 2, pacemaker 10 includes an activity sensor 20, which may be, for example, a piezoelectric element bonded to the inside of the pacemaker's shield. Such a pacemaker/activity sensor configuration is the subject of U.S. Pat. No. 4,485,813 issued to Anderson et al, which is hereby incorporated by reference in its entirety. Piezoelectric sensor 20 provides a sensor output which varies as a function of a measured parameter that relates to the metabolic requirements of patient 12.

Pacemaker 10 of FIG. 2 is programmable by means of an external programming unit (not shown in the Figures). One such programmer suitable for the purposes of the present invention is the Medtronic Model 9760 programmer which has been commercially available for several years and is intended to be used with all Medtronic pacemakers. The programmer is a microprocessor device which provides a series of encoded signals to pacemaker 10 by means of a programming head which transmits radio-frequency (RF) encoded signals to pacemaker 10 according to the telemetry system laid out, for example, in U.S. Pat. No. 4,305,397 issued to Weisbrod et al. on Dec. 15, 1981, U.S. Pat. No. 4,323,074 issued to Nelms on Apr. 6, 1982 or in U.S. Pat. No. 4,550,370 issued to Baker on Oct. 29, 1985, all of which are hereby incorporated by reference in their entirety. It is to be understood, however, that the programming methodologies disclosed in the above-referenced patents are identified herein for the purposes of illustration only, and that any programming methodology may be employed so long as the desired information is transmitted to the pacemaker. It is believed that one of skill in the art would be able to choose from any of a number of available programming techniques to accomplish this task.

The programmer facilitates the selection by a physician of the desired parameter to be programmed and the entry of a particular setting for the desired parameter. For purposes of the present invention, the specifics of operation of the programmer are not believed to be important with the exception that whatever programmer is used must include means for selecting desired pacing rates, but may also include means for selection of acceleration and deceleration parameters which limit the rate of change of the pacing rate.

Pacemaker 10 is schematically shown in FIG. 2 to be electrically coupled via a pacing lead 14 to a patient's heart 16. Lead 14 includes an intracardiac tip electrode 24 located near its distal end and positioned within the right ventricular (RV) or right atrial (RA) chamber of heart 16. Lead 14 is a bipolar electrode, as is well known in the art. Although an application of the present invention in the context of a single-chamber pacemaker will be disclosed herein for illustrative purposes, it is to be understood that the present invention is equally applicable in dual-chamber pacemakers.

Electrode 24 is coupled via lead conductor 14 through input capacitor 26 to node 28 and to input/output terminals of an input/output circuit 30. In the presently disclosed embodiment, activity sensor 20 is bonded to the inside of the pacemaker's outer protective shield, in accordance with common practice in the art. As shown in FIG. 2, the output from activity sensor 20 is coupled to input/output circuit 30.

Input/output circuit 30 contains the analog circuits for interface to the heart 16, activity sensor 20, antenna 52, as well as circuits for the application of stimulating pulses to heart 16 to control its rate as a function thereof under control of the software-implemented algorithms in a microcomputer circuit 32.

Microcomputer circuit 32 comprises an on-board circuit 34 and an off-board circuit 36. On-board circuit 34 includes a microprocessor 38, a system clock circuit 40, and on-board RAM 42 and ROM 44. In the presently disclosed embodiment of the invention, off-board circuit 36 includes a RAM/ROM unit. On-board circuit 34 and off-board circuit 36 are each coupled by a data communication bus 48 to a digital controller/timer circuit 50. Microcomputer circuit 32 may be fabricated of a custom integrated circuit device augmented by standard RAM/ROM components.

It will be understood that the electrical components represented in FIG. 2 are powered by an appropriate implantable battery power source 51, in accordance with common practice in the art. For the sake of clarity, the coupling of battery power to the various components of pacemaker 10 has not been shown in the Figures.

An antenna 52 is connected to input/output circuit 30 for purposes of uplink/downlink telemetry through RF transmitter and receiver unit 54. Unit 54 may correspond to the telemetry and program logic employed in U.S. Pat. No. 4,556,063 issued to Thompson et al. on Dec. 3, 1985 and U.S. Pat. No. 4,257,423 issued to McDonald et al. on Mar. 24, 1981, both of which are incorporated herein by reference in their entirety. Telemetering analog and/or digital data between antenna 52 and an external device, such as the aforementioned external programmer (not shown), may be accomplished in the presently disclosed embodiment by means of all data first being digitally encoded and then pulse-position modulated on a damped RF carrier, as substantially described in U.S. Pat. No. 5,127,404 issued Jul. 7, 1992, entitled "Improved Telemetry Format", which is assigned to the assignee of the present invention and which is incorporated herein by reference. The particular programming and telemetry scheme chosen is not believed to be important for the purposes of the present invention so long as it provides for entry and storage of values of rate-response parameters discussed hereinbefore.

A crystal oscillator circuit 56, typically a 32,768-Hz crystal-controlled oscillator, provides main timing clock signals to digital controller/timer circuit 50. A $V_{REF}$ and Bias circuit 58 generates stable voltage reference and bias currents for the analog circuits of input-/output circuit 30. An analog-to-digital converter (ADC) and multiplexer unit 60 digitizes analog signals and voltages to provide "real-time" telemetry intracardiac signals and battery end-of-life (EOL) replacement functions. A $\Delta Z$ Processor 100 is utilized in conjunction with output signals from impedance sensors, as described in greater detail in U.S. Pat. No. 5,271,395 issued to Wahlstrand et al. incorporated by reference hereinbefore. A power-on-reset (POR) circuit 62 functions as a means to reset circuitry and related function to a default condition upon detection of a low battery condition, which will occur upon initial device power-up or will transiently occur in the presence of electromagnetic interference, for example.

The operating commands for controlling the timing of pacemaker 10 are coupled by bus 48 to digital controller/timer circuit 50 wherein digital timers and counters are employed to establish the overall escape interval of the pacemaker, as well as various refractory, blanking, and other timing windows for controlling the operation of the peripheral components within input-/output circuit 30.

Digital controller/timer circuit 50 is coupled to sensing circuitry including a sense amplifier 64, a peak sense and threshold measurement unit 65, and a comparator/threshold detector 69. Circuit 50 is further coupled to receive an output signal from an electrogram (EGM) amplifier 66. EGM amplifier 66 receives, amplifies and processes electrical signals provided from multiplexor 84. Multiplexor 84 receives a signal from one of two places: 1) electrode 24, lead conductor 14 and capacitor 26, this signal being representative of the electrical activity of the patient's heart 16; and 2) an impedance waveform resulting from operation of an impedance circuit 82 described in detail in the 870,062 application referenced hereinbefore.

A sense amplifier 64 amplifies sensed electrical cardiac signals and provides this amplified signal to peak sense and threshold measurement circuitry 65, which provides an indication of peak sensed voltages and the measured sense amplifier threshold voltage on multiple conductor signal path 67 to digital controller/timer circuit 50. The amplified sense amplifier signal is then provided to comparator/threshold detector 69. Sense amplifier 64 may correspond, for example, to that disclosed in U.S. Pat. No. 4,379,459 issued to Stein on Apr. 12, 1983, incorporated by reference herein in its entirety. The electrogram signal developed by EGM amplifier 66 is used on those occasions when the implanted device is being interrogated by an external programmer, not shown, to transmit by uplink telemetry a representation of the analog electrogram of the patient's electrical heart activity, such as described in U.S. Pat. No. 4,556,063 referenced hereinbefore. As previously noted, EGM amplifier 66 also selectively receives an impedance waveform which may also be transmitted by uplink telemetry to an external programmer.

An output pulse generator 68 provides pacing stimuli to the patient's heart 16 through coupling capacitor 74 in response to a pacing trigger signal developed by digital controller/timer circuit 50 each time the escape interval times out, or an externally transmitted pacing command has been received, or in response to other stored commands as is well known in the pacing art. Output amplifier 68 may correspond generally to the output amplifier disclosed in U.S. Pat. No. 4,476,868 issued to Thompson on Oct. 16, 1984 also incorporated herein by reference in its entirety.

While specific embodiments of input amplifier 64, output amplifier 68, and EGM amplifier 66 have been identified herein, this is done for the purposes of illustration only. It is believed by the inventor that the specific embodiments of such circuits are not critical to the present invention so long as they provide means for generating a stimulating pulse and provide digital controller/timer circuit 50 with signals indicative of natural and/or stimulated contractions of the heart.

Digital controller/timer circuit 50 is coupled to an activity circuit 70 for receiving, processing, and amplifying signals received from activity sensor 20. Digital controller/timer circuit 50 is also coupled, via line 80 to a $\Delta Z$ Processor circuit 100, which in turn is coupled to an impedance circuit 82. Impedance circuit 82 is coupled directly to pacing lead 14. Impedance circuit 82 measures cardiac impedance by outputting periodic biphasic current pulses on pacing lead 14, and then sensing the resulting voltages. The resulting voltages are sensed and demodulated in an AC-coupled manner, to generate a voltage waveform (hereinafter "impedance waveform") which reflects changes in impedance (i.e., with baseline impedance subtracted). The utilization of an impedance sensor of this type in a cardiac pacemaker is the subject of U.S. Pat. No. 4,702,253 to Nappholz et al., which is hereby incorporated by reference in its entirety. The measured impedance changes will be related to respiratory changes in frequency and magnitude. The analog impedance waveform is scaled and filtered in impedance circuit 82, and the resulting waveform provided to $\Delta Z$ Processor 100 for conversion to digital format, as described in the 870,062 patent application referenced hereinbefore. The time-course of the impedance waveform represents the minute ventilation (MV) parameter.

Figure 3:
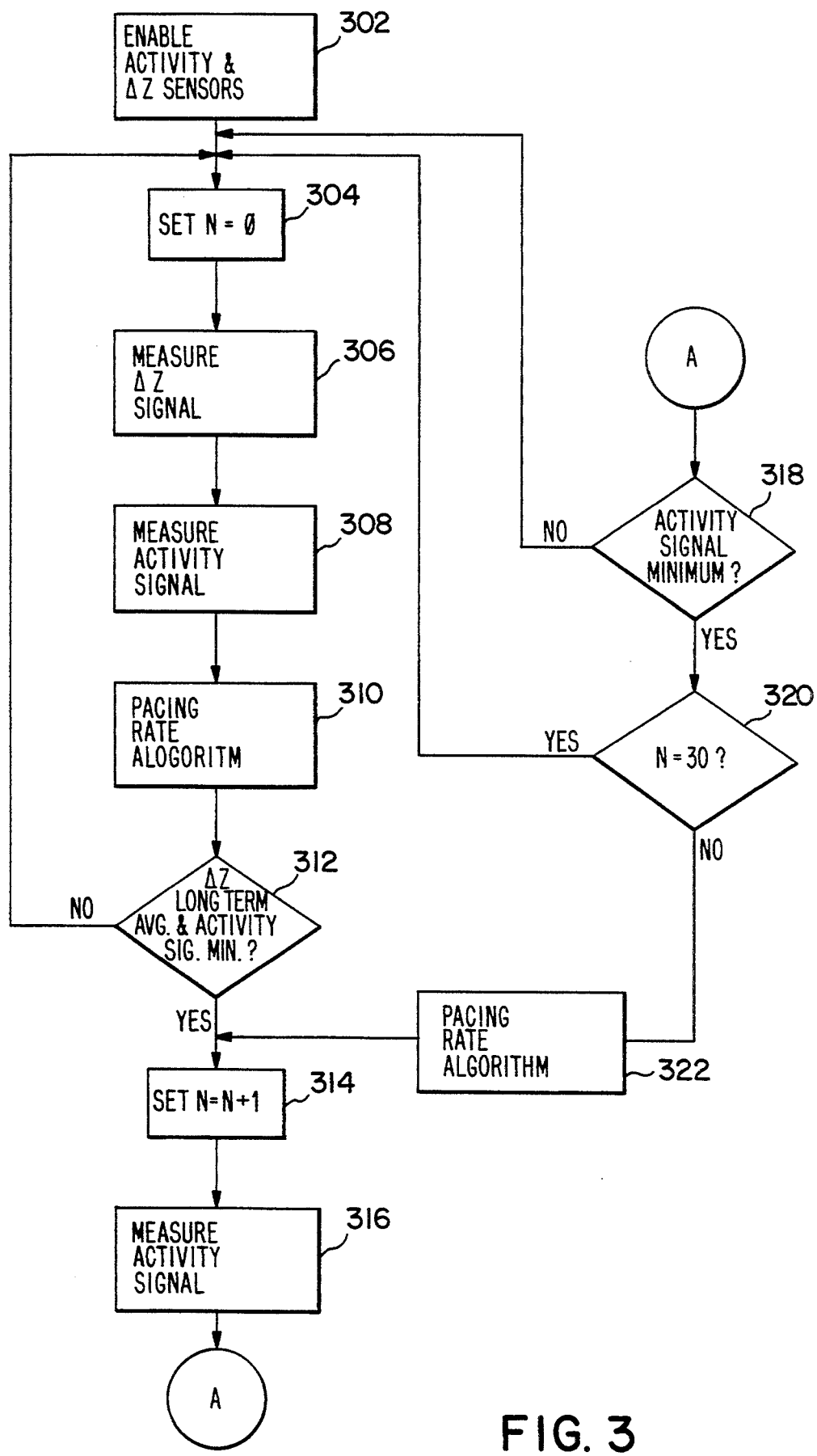
FIG. 3 is a flow diagram illustrating the process for controlling the blending of an Activity sensor signal with a Minute Ventilation sensor signal such that battery energy is optimized without degradation of the multiple-sensor behavior.

The process of controlling one sensor (i.e., Activity) by another sensor (i.e, Minute Ventilation), will best be understood with reference to the flow diagram of FIG. 3. In FIG. 3, the process begins at block 302, where the activity sensor 20 and the $\Delta Z$ Processor 100 are enabled.

Next, in block 304, a counter is initialized to zero.

In block 306, Minute Ventilation (as measured by the impedance of transthoracic or other vectors) is measured and a long term average is calculated according to an MV algorithm such as that disclosed in the '062 reference discussed hereinbefore.

In block 308, the patient's current activity level is measured before entering the pacing rate algorithm in block 310, where a target rate-responsive pacing rate based upon a function of the two measurements made in blocks 306 and 308 is computed according to a pacing rate algorithm such as that disclosed in the '062 reference discussed above.

Next, in decision block 312, a comparison is made to determine if the most recent activity level measured is at its minimum observed value and if the MV long-term average is simultaneously at its minimum. If either condition is not met, then the normal pacing rate algorithm (blending MV and activity level measurements) continues to run in its normal mode of operation. If however, both conditions are simultaneously satisfied, then the counter which was initialized in block 304, is incremented by one, and the normal pacing mode loop is broken as shown in block 316.

In block 316, the level of patient activity continues to be measured until either of two conditions are met as illustrated in blocks 318 and 320.

In block 318, the measured activity level is again compared with its minimum observed value, and if the level of patient activity continues to be at its minimum, then another comparison is made in block 320. In block 320, the current count value stored in the counter is examined to see if 30 measurement cycles have passed without taking any MV measurements. If not, then the pacing rate algorithm continues to run, using as inputs, the minimum activity level and minimum long-term average ΔZ measurements. If, however, the most current level of patient activity measured in block 316 is no longer at its observed minimum level as indicated by the "NO" decision in decision block 318, then the new pacing rate will be determined not only by the activity signal, but also by a new measured value for the MV long-term average by entering the pacing rate algorithm through block 304 as indicated in FIG. 3.

In the alternative, if the activity level remains at its minimum level as indicated by a "YES" decision in decision block 318, then the counter is checked to determine its present count value as discussed hereinbefore. The present inventive method uses a count value of 30 to eliminate up to 30 consecutive scheduled two-second samples of MV raw data. This value has been found to be effective in making a substantial improvement in battery longevity without impairing the performance of a multiple sensor cardiac pacemaker which blends the outputs of the multiple sensors to produce a composite heart rate. It can be seen in decision block 320 that once the counter reaches a count value of 30, that the normal pacing rate algorithm continues to run by again entering through block 304 where the counter is again initialized to zero, and where the pacing rate is again calculated based on inputs from both activity measurements and ΔZ measurements.

It is important to note that the embodiment described hereinbefore ensures that the MV sensor will be sampled at least once per minute, even if the Activity sensor remains at its minimum value.

While a specific embodiment of a cardiac pacemaker and method of operation has been identified herein, this is done for the purposes of illustration only. One skilled in the art will appreciate that the invention is not necessarily so limited. It will thus be understood that numerous other embodiments, examples, uses, modifications of, and departures from the teachings disclosed may be made, without departing from the scope of the present invention as claimed herein. For example, it is believed by the inventor that the specific embodiment of such a pacemaker and related method of operation is not critical to the present invention so long as it provides means for controlling one physiological sensor by another physiological sensor for the purpose of conserving battery energy without impairing the benefits obtained from blending the outputs from the multiple physiological sensors.

What is claimed is:

1. A method of pacing a patient's heart, comprising the steps of:
   (a) applying a respiration sensor which provides a respiration signal indicative of respiratory activity to said patient and activating said respiration sensor to produce said respiration signal;
   (b) applying an activity sensor which provides an activity signal indicative of physical activity to said patient and activating said activity sensor to produce said activity signal;
   (c) computing an average value of said respiration signal over a predetermined interval;
   (d) comparing said activity signal and said average value with minimum values;
   (e) delivering cardiac pacing pulses to said heart at a rate determined as a function of said activity signal and said respiration signal, when said activity signal and said average value are not at or below said minimum values simultaneously; and
   (f) disabling said respiration sensor when said activity signal and said average value are at or below said minimum values, simultaneously.

2. A pacemaker, enclosed within a housing, comprising:
   (a) a rate control circuit means for producing triggering signals at a rate varying between predetermined upper and lower pacing rates;
   (b) a pulse generator means, coupled to said rate control circuit means, for generating a pacing pulse responsive to a triggering signal from said rate control circuit means;
   (c) an activity sensor means for producing an activity signal indicative of patient activity;
   (d) respiration sensor means for producing a respiration signal indicative of patient respiration, said rate control circuit means responsive to said activity signal and said respiration signal for varying said rate of said triggering signals and;
   (e) processing means, coupled to said activity sensor means, said respiration sensor means, and said rate control circuit means, for comparing each of said activity signal and said respiration signal with a corresponding minimum values, and for producing a disable signal representative of a condition wherein said activity signal and said respiration signal are simultaneously equivalent to or less than said corresponding minimum values; and means for disabling said respiration sensor in response to said disable signal.

3. A cardiac pacemaker, comprising:
   first sensor means for measuring a first physiologic parameter of a patient;
   second sensor means for measuring a second physiologic parameter of said patient, said second sensor means consuming less energy when activated than said first sensor means;

pulse generator means for generating pacing pulses at a pacing rate;

control means for determining said pacing rate as a function of said first measured physiologic parameter; and means for inactivating said first sensor means in response to both said first and second measured physiologic parameters falling below predetermined minimum values.

4. A pacemaker according to claim 3 further comprising means for activating said first sensor means in response to said second measured physiologic parameter exceeding a predetermined value.

5. A pacemaker according to claim 3 or claim 4 wherein said control means comprises means for activating said first sensor means in response to said first sensor means being inactivated for an extended period.

6. A pacemaker according to claim 5 wherein said control means comprises means for activating said first sensor means in response to said first sensor means being inactivated for a predetermined period of time.

7. A pacemaker according to claim 3 wherein said first sensor means comprises means for measuring an average value of said first physiologic parameter over a predefined time period, and wherein said inactivating means comprises means for inactivating said first sensor means in response to both said measured average value and said second measured physiologic parameter falling below predetermined minimum values.

8. A pacemaker according to claim 3 wherein said first sensor means comprises a means for measuring respiratory activity of a patient and wherein said second sensor means comprises means for measuring physical activity of said patient.

9. A cardiac pacemaker, comprising:
a first sensor means for measuring a first physiologic parameter of a patient;
a second sensor means for measuring a second physiologic parameter of said patient, said second sensor means consuming less energy when activated than said first sensor means;
pulse generator means for generating pacing pulses at a pacing rate;
control means for determining said pacing rate as a function of said first measured physiologic parameter;
means coupled to said first sensor means for inactivating said first sensor means; and
means for activating said first sensor means in response to said first sensor means being inactivated for an extended period.

10. A pacemaker according to claim 9 wherein said activating means comprises means for activating said first sensor means in response to said first sensor means being inactivated for a predetermined period of time.

11. A pacemaker according to claim 9 wherein said inactivating means comprises means for inactivating said first sensor means in response to both said first and second measured physiologic parameters falling below predetermined minimum values.

12. A pacemaker according to claim 9 or claim 10 or claim 11 wherein said first sensor means comprises means for measuring respiratory activity of a patient and wherein said second sensor means comprises means for measuring physical activity of said patient.

13. A method of pacing a patient's heart, comprising:
applying a first sensor which measures a first physiologic parameter to said patient and activating said first sensor to measure said first physiologic parameter;
applying a second sensor which measures a second physiologic parameter of said patient, said second sensor consuming less energy when activated than said first sensor, and activating said second sensor to measure said second physiologic parameter;
generating pacing pulses at a pacing rate;
determining said pacing rate as a function of said first measured physiologic parameter; and
inactivating said first sensor in response to both said first and second measured physiologic parameters falling below predetermined minimum values.

14. A method according to claim 13 further comprising activating said first sensor in response to said second measured physiologic parameter exceeding a predetermined value.

15. A method according to claim 13 or claim 14 further comprising activating said first sensor in response to said first sensor being inactivated for an extended period.

16. A method according to claim 15 wherein said activating step comprises activating said first sensor in response to said first sensor being inactivated for a predetermined period of time.

17. A method according to claim 13 wherein said step of measuring said first physiologic parameter comprises measuring an average value of said first physiologic parameter over a predefined time period, and wherein inactivating step comprises inactivating said first sensor in response to both said measured average value and said second measured physiologic parameter falling below predetermined minimum values.

18. A method according to claim 13 wherein said step of measuring said first physiologic parameter comprises measuring respiratory activity of a patient and wherein said step of measuring said second physiologic parameter comprises measuring physical activity of said patient.

19. A method of pacing a patient's heart, comprising:
applying a first sensor which measures a first physiologic parameter, to said patient and activating said first sensor to measure said first physiologic parameter;
applying a second sensor which measures a second physiologic parameter, to said patient, said second sensor consuming less energy when activated than said first sensor and activating said second sensor to measure said second physiologic parameter;
generating pacing pulses at a pacing rate;
determining said pacing rate as a function of said first measured physiologic parameter;
after said determining step, inactivating said first sensor; and
thereafter activating said first sensor in response to said first sensor being inactivated for an extended period.

20. A method according to claim 19 wherein said activating step comprises activating said first sensor in response to said first sensor being inactivated for a predetermined period of time.

21. A method according to claim 19 wherein said inactivating step comprises inactivating said first sensor in response to both said first and second measured physiologic parameters falling below predetermined minimum values.

22. A method according to claim 19 or claim 20 or claim 21 wherein said step of measuring said first physiologic parameter comprises measuring respiratory activity of a patient and wherein said step of measuring said second physiologic parameter comprises measuring physical activity of said patient.

* * * * *